UnitedStates Patent
Pinkhassik et al.

(10) Patent No.: US 9,248,441 B2
(45) Date of Patent: Feb. 2, 2016

(54) POLYMER NANOCAPSULES ENTRAPPING METAL NANOPARTICLES

(75) Inventors: Eugene Pinkhassik, Clayton, MO (US); Sergey Shamakov, St. Louis, MO (US)

(73) Assignee: University of Memphis Research Foundation, Memphis, TN (US)

( * ) Notice: Subject to any disclaimer, the term of this patent is extended or adjusted under 35 U.S.C. 154(b) by 61 days.

(21) Appl. No.: 13/820,085

(22) PCT Filed: Aug. 31, 2011

(86) PCT No.: PCT/US2011/050109
§ 371 (c)(1),
(2), (4) Date: May 13, 2013

(87) PCT Pub. No.: WO2012/031053
PCT Pub. Date: Mar. 8, 2012

(65) Prior Publication Data
US 2013/0237408 A1 Sep. 12, 2013

Related U.S. Application Data

(60) Provisional application No. 61/378,934, filed on Aug. 31, 2010.

(51) Int. Cl.
| | |
|---|---|
| *C08K 3/10* | (2006.01) |
| *C08K 3/08* | (2006.01) |
| *B01J 35/02* | (2006.01) |
| *A61K 9/50* | (2006.01) |
| *B01J 13/14* | (2006.01) |
| *B82Y 30/00* | (2011.01) |
| *B82Y 40/00* | (2011.01) |
| *A61K 9/127* | (2006.01) |
| *A61K 33/00* | (2006.01) |

(52) U.S. Cl.
CPC ............... *B01J 35/026* (2013.01); *A61K 9/127* (2013.01); *A61K 9/50* (2013.01); *A61K 33/00* (2013.01); *B01J 13/14* (2013.01); *B82Y 30/00* (2013.01); *B82Y 40/00* (2013.01)

(58) Field of Classification Search
CPC ...................................................... B01J 35/026
USPC ........................................................ 524/403
See application file for complete search history.

(56) References Cited

U.S. PATENT DOCUMENTS

2006/0167147 A1    7/2006  Asgari
2009/0053512 A1    2/2009  Pyun et al.

OTHER PUBLICATIONS

Kim et al., Nano Letters, 2(12), 1383-1387, 2002.*
Wu et al., Angew. Chem. Int. Ed., 48, 3842-3845, 2009.*
Li et al., Macromol. Rapid Commun., 30, 188-193, 2009.*
Kim et al., Nano Letters, vol. 2, No. 12, 1383-1387, 2002.*
Kim et al., "Synthesis of Nanorattles Composed of Gold Nanoparticles Encapsulated in Mesoporous Carbon and Polymer Shells," Nano Letters, 2(12): 1383-1387 (2002).
Chen et al., "Enhanced Stability and Bioconjugation of Photo-Cross-Linked Polystyrene-Shell, Au-Core Nanoparticles," Langmuir, 23(14):7491-7497 (2007).
Shmakov et al., "Simultaneous templating of polymer nanocapsules and entrapped silver nanoparticles", Chem. Commun. 46:7346-7348 (2010).
International Search Report and Written Opinion mailed Apr. 27, 2012, in corresponding PCT Application No. PCT/US2011/050109.

* cited by examiner

*Primary Examiner* — Hui Chin
(74) *Attorney, Agent, or Firm* — Mintz Levin Cohn Ferris Glovsky and Popeo, P.C.; Peter F. Corless; Carolina E. Säve

(57) ABSTRACT

Metal nanoparticles entrapped or encapsulated in a polymer nanocapsule disclosed. Methods of making and using the metal nanoparticles entrapped or encapsulated in a polymer nanocapsule are also disclosed.

20 Claims, 3 Drawing Sheets

POLYMER NANOCAPSULES ENTRAPPING METAL NANOPARTICLES

CROSS-REFERENCE TO RELATED APPLICATION

This application is the U.S. national phase application pursuant to 35 U.S.C. §371 of PCT International Patent Application No. PCT/US2011/050109, filed Aug. 31, 2011, which claims the benefit of priority to U.S. Provisional Patent Application No. 61/378,934, filed Aug. 31, 2010. The entire contents of the aforementioned patent applications are incorporated herein by reference.

STATEMENT OF RIGHTS TO INVENTIONS MADE UNDER FEDERALLY SPONSORED RESEARCH

This work was supported by grants from the National Science Foundation (Grant Nos. CHE-1012951, DMR-0521226, and CHE-0349315) and National Institutes of Health (Grant No. 1R01HL079147-01). The government has certain rights in the invention.

BACKGROUND OF THE INVENTION

Designing economical synthesis of complex nanostructures is increasingly important for practical applications of nanoscale objects. Nanoparticles have demonstrated tremendous promise in many applications, such as catalysis,[1] medical imaging,[2] and development of new analytical methods.[3] Nanoparticle-phospholipid hybrids have been used for in vivo imaging and drug delivery.[4]

SUMMARY OF THE INVENTION

The invention provides a metal nanoparticle entrapped or encapsulated in a polymer nanocapsule, and method for making and using the metal nanoparticle entrapped in a polymer nanocapsule.

In one aspect, the invention provides a metal nanoparticle entrapped or encapsulated in a polymer nanocapsule. In certain embodiments, the metal nanoparticle is a metal selected from the group consisting of silver, platinum, palladium, and gold. In certain embodiments, the metal nanoparticle is silver. In certain embodiments, the polymer nanocapsule is a copolymer of a styrene with divinylbenzene. In certain embodiments, the polymer nanocapsule is a copolymer of tert-butylstyrene with divinylbenzene.

In another aspect, the invention provides a method of preparing a metal nanoparticle entrapped or encapsulated in a polymer nanocapsule, the method comprising polymerizing monomers to form the polymer nanocapsule and simultaneously forming the metal nanoparticle. In certain embodiments, the monomers are polymerized using a free-radical initiator. In certain embodiments, the monomers are polymerized in a lipid bilayer. In certain embodiments, the lipid bilayer is a lipid bilayer of a liposome. In certain embodiments, the method further comprises the step of removing the lipid bilayer after synthesis of the metal nanoparticle entrapped in a polymer nanocapsule.

DETAILED DESCRIPTION OF THE INVENTION

Figure 1:
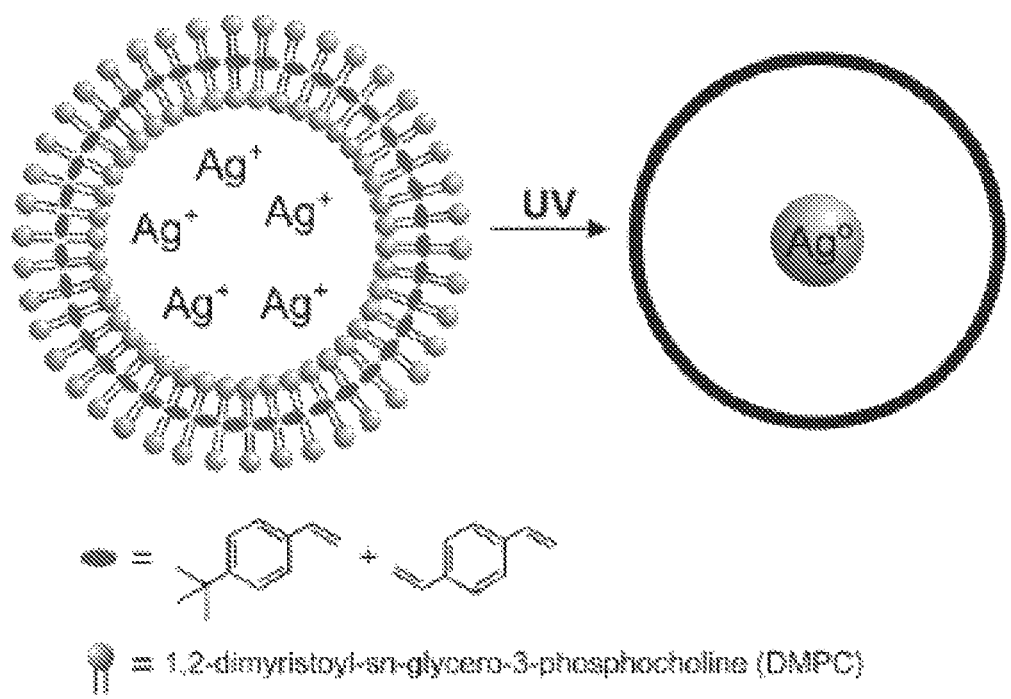
FIG. 1 shows a simultaneous synthesis of polymer nanocapsules and entrapped silver nanoparticles. Both reactions are facilitated by a free-radical photoinitiator.

As used herein, the term "nanoparticle" refers to a nanoscale metallic particle. Nanoparticles can be, e.g., about 0.5 nm to about 20 nm in size. Nanoparticles can be of varying shapes, such as spherical or spheroidal.

As used herein, the term "nanocapsule" refers to a hollow polymeric shell or enclosure having an outer shell wall defining an interior space. Nanocapsules can be, e.g., about 40 nm to about 50 microns in size. Nanocapsules can be of varying shapes, such as spherical or spheroidal.

In one aspect, the invention provides a metal nanoparticle entrapped or encapsulated in a polymer nanocapsule. In certain embodiments, the metal nanoparticle is a metal selected from the group consisting of silver, platinum, palladium, and gold. In certain embodiments, the metal nanoparticle is silver. In certain embodiments, the polymer nanocapsule is a copolymer of a styrene with divinylbenzene. In certain embodiments, the polymer nanocapsule is a copolymer of tert-butylstyrene with divinylbenzene. In certain embodiments, the nanocapsule has a size in the range of 40-120 nm. In certain embodiments, the metal nanoparticle has a size of about 1-10 nm, more preferably about 5-6 nm, most preferably about 5.5 nm. In certain embodiments, the polymer nanocapsule further includes or entraps a drug or therapeutic agent (e.g., a chemotherapeutic agent).

In another aspect, the invention provides a method of preparing a metal nanoparticle entrapped or encapsulated in a polymer nanocapsule, the method comprising polymerizing monomers to form the polymer nanocapsule and simultaneously forming the metal nanoparticle. In certain embodiments, the monomers are polymerized using a free-radical initiator. In certain embodiments, the monomers are polymerized in a lipid bilayer. In certain embodiments, the lipid bilayer is a lipid bilayer of a liposome. In certain embodiments, the metal nanoparticle is formed by free-radical reduction of a metal ion dissolved in an aqueous solvent phase. In certain embodiments, the method further comprises the step of removing the lipid bilayer after synthesis of the metal nanoparticle entrapped in a polymer nanocapsule.

In another aspect, the invention provides a method of preparing a metal nanoparticle entrapped in a polymer nanocapsule, the method comprising providing an aqueous phase containing vesicles, wherein the aqueous phase includes a metal ion or salt and the vesicles comprise at least one monomer; and polymerizing the at least one monomer to form the polymer nanocapsule and simultaneously forming the metal nanoparticle entrapped in the polymer nanocapsule. In certain embodiments, the at least one monomer is polymerized using a free-radical initiator. In certain embodiments, the at least one monomer is polymerized in a lipid bilayer of the vesicles. In certain embodiments, the lipid bilayer is a lipid bilayer of a liposome. In certain embodiments, the metal nanoparticle is formed by free-radical reduction of a metal ion dissolved in an aqueous solvent phase. In certain embodiments, the method further comprises the step of removing the lipid bilayer after synthesis of the metal nanoparticle entrapped in a polymer nanocapsule.

In another aspect, the invention provides methods of using a metal nanoparticle entrapped or encapsulated in a polymer nanocapsule. Entrapment of metal nanoparticles in hollow nano-capsules may offer several advantages. Nanoparticles may be stabilized without the need for surfactants. Adequate space separation of nanoparticles will ensure maximum efficiency of nanoparticles in catalysis and sensor applications. Therapeutic agents may be co-encapsulated with nanoparticles that would act as radiographic contrasts. This approach may offer high loading capacity for carrying drugs, which is important for either delivering high doses of medication or enabling extended release. Several examples of "nanorattles" have been reported.[5] Decreasing the shell thickness in these hybrid nanostructures is important for their practical applications.

In another aspect, the invention provides a metal nanoparticle entrapped or encapsulated in a polymer nanocapsule produced by any method described herein.

In another aspect, the invention provides a metal nanoparticle entrapped or encapsulated in a polymer nanocapsule, optionally further comprising a therapeutic agent (e.g., a chemotherapeutic agent), for use in therapy.

In another aspect, the invention provides a metal nanoparticle entrapped or encapsulated in a polymer nanocapsule, optionally further comprising a therapeutic agent (e.g., a chemotherapeutic agent), for preparation of a medicament for the treatment of a disease or condition such as cancer.

Thus, for example, nanocapsules can be used as nanoreactors. Many metal nanoparticles showed significant catalytic activity. It is hard to create catalytic devices from nanoparticles because nanoparticles tend to aggregate due to their high surface area and corresponding high surface energy. They need to be stabilized by either surrounding them with a surfactant matrix of by embedding them in polymers. As a result, they either lose much of their catalytic activity and/or show slow interactions with substrates. Entrapping nanoparticles in hollow nanocapsule keeps the naked nanoparticles apart and provides enough empty space around them for the flow of substrates and products.

As another example, the nanocapsules can be used in nanosensors. Silver nanoparticles have been used in recently-emerged surface-enhanced raman scattering (SERS) method. Adsorption of molecules on the surface of silver nanoparticles result in dramatic signal enhancement, allowing detection of very small amounts of analytes. Analysis of a complex mixture is complicated though, because all molecules would have increased signals. If silver nanoparticles are entrapped in nanocapsules with selective pores, only certain molecules would adsorb on the nanoparticles. This would permit more accurate measurements of small molecules in physiological fluids (blood), where large molecules such as proteins or DNA would be filtered out by the nanocapsules.

Nanocapsules entrapping metal nanoparticles can be prepared, e.g., as described herein. Here we show a one-step synthesis of hollow polymer nanocapsules that entrap simultaneously formed silver nano-particles. We used liposomes as the scaffold for the synthesis (FIG. 1). FIG. 1 is a schematic depiction of a synthesis of a polymer nanocapsule entrapping silver nanoparticles.

In certain embodiments, a polymer nanocapsule as described herein is about 40 nm to about 50 microns in size; in certain embodiments, from about 40 nm to about 1000 nm in size; in certain embodiments, from about 40 nm to about 250 nm in size; or, in certain embodiments, from about 40 nm to about 120 nm in size. The size of the nanoparticles can be varied by changing the liposome diameter.

The polymer nanocapsule as described herein defines a shell or wall enclosing a hollow interior space (which can accommodate a metal nanoparticle and may be filed with solvent and the like). The shell or wall can be porous or permeable; the size of any pores should be small enough to retain the metal nanoparticle (i.e., to prevent the metal nanoparticle from passing out of the interior of the nanocapsule), but can be large enough to allow efficient exchange of solutes, reagents, substrates, analytes, or other small molecular species to pass across the wall between the bulk solution phase and the interior of the nanocapsule. Bilayer-templated nanocapsules can be imprinted with nanopores having controlled size, density, and chemical environment.[6] Formation of nanopores is done using pore-forming templates that are co-dissolved with monomers within the bilayer interior and that are removed after the polymerization.[6]

In certain embodiments, the polymer nanocapsule is cross-linked. The degree of cross-linking can be varied by controlling the concentration of the monomer or monomers in the lipid bilayer, the concentration of the free-radical initiator, the length of time the cross-linking polymerization reaction is perfumed, and the like.

In certain embodiments, a metallic nanoparticle (entrapped in a polymer nanocapsule) as described herein is generally from about 0.5 nm to about 50 nm in size (on average); in certain embodiments, from about 1 nm to about 20 nm in size; in certain embodiments, from about 2 nm to about 10 nm in size; or, in certain embodiments, about 5.5 nm in size (on average). The size of the metallic nanoparticle formed will depend at least in part on factors such as the amount and concentration of the metal salt in the aqueous phase in the interior of the vesicle prior to reduction of the metal ion; the size of the vesicle; the reaction time for the redox chemistry of the metal to occur, and the like. In general, larger vesicles can accommodate larger metal nanoparticles; for example, a metallic nanoparticle 50 nm in size could be formed in a vesicle 10 microns in size.

Liposomes have two distinct regions: the aqueous core and the hydrophobic bilayer interior. The hydrophobic bilayer interior of a liposome can be used for templating of nanocapsules and related structures.[6,7] Ultra-fast mass transfer across nanometer-thin walls has been used for controlling the size and chemical environment of nanopores imprinted in the bilayer-templated capsules.[6] An aqueous core has been used for templating of a broad range of nanoparticles.[8]

The present invention relates, at least in part, to the discovery that the synthesis of silver nanoparticles in the aqueous core of liposomes can be combined with the synthesis of polymer nanocapsules within the bilayer. Previously, photochemical reduction of silver, as well as other metals, was reported.[9] We have now found that a free-radical photochemical initiator, which is used to promote the polymerization the bilayer, also facilitates the growth of nano-particles in the aqueous core.

The polymer nanocapsules of the invention can be prepared using a variety of material and methods, some of which are known in the art. In general, polymer nanocapsules are formed by polymerization of one or more monomers, wherein the one or more monomers are distributed in a lipid bilayer of a scaffold, such as a vesicle (e.g., a lipid vesicle, a liposome, etc.). An aqueous phase containing vesicles such as liposomes is prepared, e.g., by hydrating lipids or other vesicle-forming reagents; monomers for polymerization can be added to the lipids or a separate solution of monomers can be added to a pre-formed liposome preparation. Metal ions are dissolved in the aqueous phase (e.g., by combining a metal salt or salts with the lipids prior to formation of vesicles in the aqueous phase, or by adding the metal salt, or a solution of metal salt, to the pre-formed liposome preparation. The photoinitiator can be added separately or together with another component (e.g., lipid, metal salt, and the like). Once the vesicle-containing preparation is formed, including the monomer(s), the metal salt, and the photoinitiator, metal nanoparticles entrapped in polymer nanocapsules can be formed by irradiation with light at a wavelength suitable to activate the photoinitiator (e.g., ultraviolet (UV) light, such as light at about 254 nm). The metal nanoparticles entrapped in polymer nanocapsules can then be isolated and purified if desired, as described herein.

Suitable monomers can be, for example, any monomers used for free-radical polymerization, such as compounds containing one or more carbon-carbon double bonds; such alkenyl compounds can be polymerized, e.g., by free radical polymerization to prepare polymeric (including co-polymeric) nanocapsules. Exemplary monomeric compounds include a styrene or styrene derivative (including t-butylstyrene and divinylbenzene) and acrylates (such as acrylic esters and methacrylic esters including butylmethacylate, tert-butylmethacrylate, ethylene glycol dimethacrylate, and the like). Examples of suitable binary copolymer systems include tert-butylstyrene and divinylbenzene, tert-butylmethacrylate and ethylene glycol dimethacrylate, butylmethacrylate and ethylene glycol dimethacrylate, and the like. Ternary and higher copolymers can also be prepared.

Polymerization of monomers can be initiated using initiators such as free radical initiators or photoinitiators (such as 2,2-dimethoxy-2-phenylacetophenone). Other free radical initiators or photoinitiators known in the art can be used. Water-soluble initiators or hydrophobic initiators can be used in order to independently vary concentration and nature of ions in the aqueous core and hydrophobic monomers in the bilayer. The amount of photoinitiator to use can be determined by one of ordinary skill in the art; in certain embodiments, the starting monomer:initiator ratio can be, e.g., 50:1 to 500:1, more preferably about 200:1.

Preparation of polymer nanocapsules of the invention can be performed at any suitable temperature, e.g., at a temperature from about 0° C. to about 100° C., more preferably from about 20° C. to about 50° C. The temperature selected will depend on factors such as the monomer(s) to be polymerized, the solvent system selected (e.g., the temperature will generally be between the freezing and boiling points of the solvent), the liposome components, and the like.

In general, polymer nanocapsules of the invention are prepared using a lipid bilayer as a "template" for polymerization of the nanocapsule "shell". In certain embodiments, the lipid bilayer is a lipid bilayer of a vesicle in an aqueous solution; vesicles include liposome. The term "liposome" as used herein includes conventional unilamellar liposomes (having a lipid bilayer and an aqueous phase in the interior). Other bilayer vesicle-like structures can be used as a template, including polymersomes prepared from diblock copolymers.

In certain embodiments, vesicles such as liposomes are prepared by methods known in the art. Exemplary classes of lipid components that form liposomes, including unilamellar liposomes, in aqueous environments are known in the art and can be selected by one of ordinary skill in the art using no more than routine experimentation. Examples of liposome-forming materials include phosphatidylcholine and derivatives, such as DMPC, and other amphiphiles that form vesicles (including dioctadecyldimethylammonium chloride and other dialkyldimethylammonium salts).

The preparation of the polymer nanocapsules of the invention can be performed in aqueous solutions, which can optionally include water-miscible organic solvents, which are generally selected to maintain complete miscibility with water (single liquid phase or monophase) under the conditions chosen, e.g., over the entire range from about 0.01 vol. % up to about 60 vol. %. Examples of water-miscible organic solvents include alcohols and aprotic solvents. Examples of alcohol solvents include methanol, ethanol, 1-propanol, 2-propanol, 2-butanol, tert-butanol, ethylene glycol, diethylene glycol, propylene glycol, glycerol, methylcellosolve (ethylene glycol monomethyl ether), methylcarbitol (diethylene glycol monomethyl ether) and the like. Methanol, ethanol or tert-butanol are preferred, particularly ethanol. Aprotic solvents include an ether, an ester, a ketone, a nitrile, an amide, or a sulfoxide. The aprotic solvent is preferably ethylene glycol dimethyl ether, ethylene glycol diethyl ether, diethyleneglycol dimethyl ether, dioxane, tetrahydrofuran, acetone, methylethylketone, acetonitrile, dimethylformamide, or dimethylsulfoxide. Other solvents include amines (e.g., butylamine) and organic acids (e.g., acetic acid). In addition, buffers and other additives may be used, e.g., as is known in the art.

The metal nanoparticle can be selected from a variety of metals, e.g., silver, platinum, palladium, and gold. In general, a desired metal nanoparticle can be formed provided that the elemental metal does not substantially react with the solvent system, e.g., does not react with water or aqueous solvent systems. One of ordinary skill in the art can select a suitable metal according to the intended use of the nanocapsules, e.g., as catalysts, as therapeutic agents, as sensors, and the like. To prepare metal nanoparticles entrapped in a polymeric nanocapsule, the metal is generally provided as a metal salt (with a metal cation) in the aqueous phase (the metal salt must have at lest some water solubility). The metal ion is then reduced to an elemental metal nanoparticle in situ through the use of free-radical redox chemistry. The metal salt selected will vary according to factors such as the desired metal nanoparticle and the solubility of the salt in the aqueous phase. For example, silver nitrate can be used for preparation of silver nanoparticles; gold salts such as gold chloride ($HAuCl_4$) can be used to prepare gold nanoparticles. Mixed metallic particles can also be prepared by use of mixtures of metal salts.

Selection of an appropriate free-radical initiator for use in the redox chemistry of the metal and for initiation of polymerization is also possible for the skilled artisan in view of the disclosure herein. Separate initiators can be used for the formation of metal nanoparticles and for the synthesis of nanocapsules, if desired.

EXAMPLES

Chemicals

All solvents used were HPLC grade. 1,2-dimyristoyl-sn-glycero-3-phosphocholine (DMPC) was purchased from Avanti Polar Lipids, Inc. as a dry powder. p-divinylbenzene (DVB), tert-Butylstyrene (tBuSt), methanol and Sephadex G-50 (medium) were purchased from Sigma-Aldrich. DVB and tBuSt were passed through an alumina column to remove the inhibitor. Sephadex G-50 (10 g) was swollen in 120 mL of water in a glass screw-capped bottle for at least 5 h at room temperature and stored at 4° C. until required for use. All other chemicals were not further purified before use.

X-Ray Diffraction Measurements

For XRD study nanocapsules were resuspended in benzene, and freeze-dried.

XRD spectra were collected on a Bruker D8 Advance X-ray diffractometer using Cu Ka radiation at 40 kV and 40 mA. The diffraction patterns were obtained in the $2\theta$ scan range 30-75° with a step size of 0.05 and a time/step of 0.2 s.

Transmission Electron Microscopy (TEM)

TEM images were acquired on a JEOL JEM1200EXII microscope. Samples were negatively stained with phosphotungstic acid (pH 5.9) on a carbon grid.

Dynamic Light Scattering (DLS)

Hydrodynamic diameter measurements were performed on a Malvern Nano-ZS zetasizer (Malvern Instruments Ltd., Worcestershire, U.K.). The Helium-Neon laser, 4 mW, operates at 633 nm, with the scatter angle fixed at 173°, and the temperature at 25° C. 80 µL samples were taken from the reaction vials with a pipet and were placed into disposable cuvettes without dilution (70 µL, 8.5 mm center height Brand UV-Cuvette micro). At least 10 scans were collected from each sample.

UV/VIS Spectroscopy

UV spectra were recorded on Agilent Technologies 8453 UV spectrophotometer in quartz cuvette in the range 200-700 nm. Molar extinction coefficient ($\epsilon$) for 2,2-dimethoxy-2-phenylacetophenone in MeOH was determined (at $\lambda max=253$ nm) to be $12200\pm100$ L mol$^{-1}$ cm$^{-1}$.

Example 1

Synthesis of Nanocapsules with Entrapped Silver Nanoparticles

Nanocapsules with entrapped silver nanoparticles were prepared by the following procedure: tert-Butylstyrene (24 µL, $1.33\times10^{-5}$ mol), p-divinylbenzene (19 µL, $1.33\times10^{-5}$ mol), and 2,2-dimethoxy-2-phenylacetophenone, DMPA, (UV initiator; 0.33 mg, $1.3\times10^{-6}$ mol) were added to a solution of DMPC (60 mg, $8.85\times10^{-5}$ mol) in CHCl$_3$. The monomers were purified on a column of neutral alumina prior to addition. The CHCl$_3$ was evaporated using a stream of purified argon to form a lipid-monomer film on the wall of a culture tube. The film was further dried under vacuum for 30 min to remove traces of CHCl$_3$. The dried film was hydrated with $10^{-2}$ mol solution of AgNO$_3$ in deionized water to give a dispersion of multilamellar vesicles, which was then extruded at 35° C. through a polycarbonate Nucleopore track-etch membrane (Whatman) with 0.1-m pore size using a Lipex stainless steel extruder (Northern Lipids). Prior to polymerization, unloaded silver ions were removed from the mixture by size-exclusion chromatography on Sephadex G-50 column. Oxygen was removed by passing purified argon through the solution. The sample was irradiated ($\lambda=254$ nm) in a photochemical reactor equipped with a stirrer (10 lamps of 32 W each; 10-cm distance between the lamps and the sample) for 60 min. Methanol (10 mL) was added, and the precipitate was washed 3-5 times with methanol. For DLS measurements and UV-spectroscopy prepared nanocapsules were resuspended in Triton X-100 solution in water (0.5 mL, 2%) by stirring for 1 h at ambient temperature.

As described above, liposomes containing monomers (1:1 mixture of tert-butylstyrene and divinylbenzene) and a photoinitiator (2,2-dimethoxy-2-phenylacetophenone, DMPA) in the bilayer and silver ions in the aqueous core are prepared by hydrating a mixture of lipids and monomers with the aqueous solution of silver nitrate followed by extrusion. The sample is then irradiated with UV light to initiate both the polymerization and formation of nanoparticles. The formation of nano-particles is evidenced by the yellow color due to surface plasmon resonance. Polymerization was typically complete within one hour. The rate of polymerization is consistent with previous kinetic studies of styrene polymerization in micro-emulsions and self-assembled monolayers.[10]

In these Examples, the total amount of photoinitiator was approximately 1.5 times greater than the amount of silver ions entrapped within liposomes. The starting monomer:initiator ratio was 200:1.

After the synthesis, the lipid scaffold can be removed by either precipitation and washing with methanol or by using surfactants, such as Triton X-100 or sodium dodecyl sulfate (SDS).

When surfactants are used, nanocapsules are solubilized in water. Precipitation from methanol can be followed by freeze-drying from benzene and subsequent resuspension in organic solvents. Capsules can be freeze-dried and stored for an extended period of time before resuspension in organic solvents or water.[6]

Figure 2:
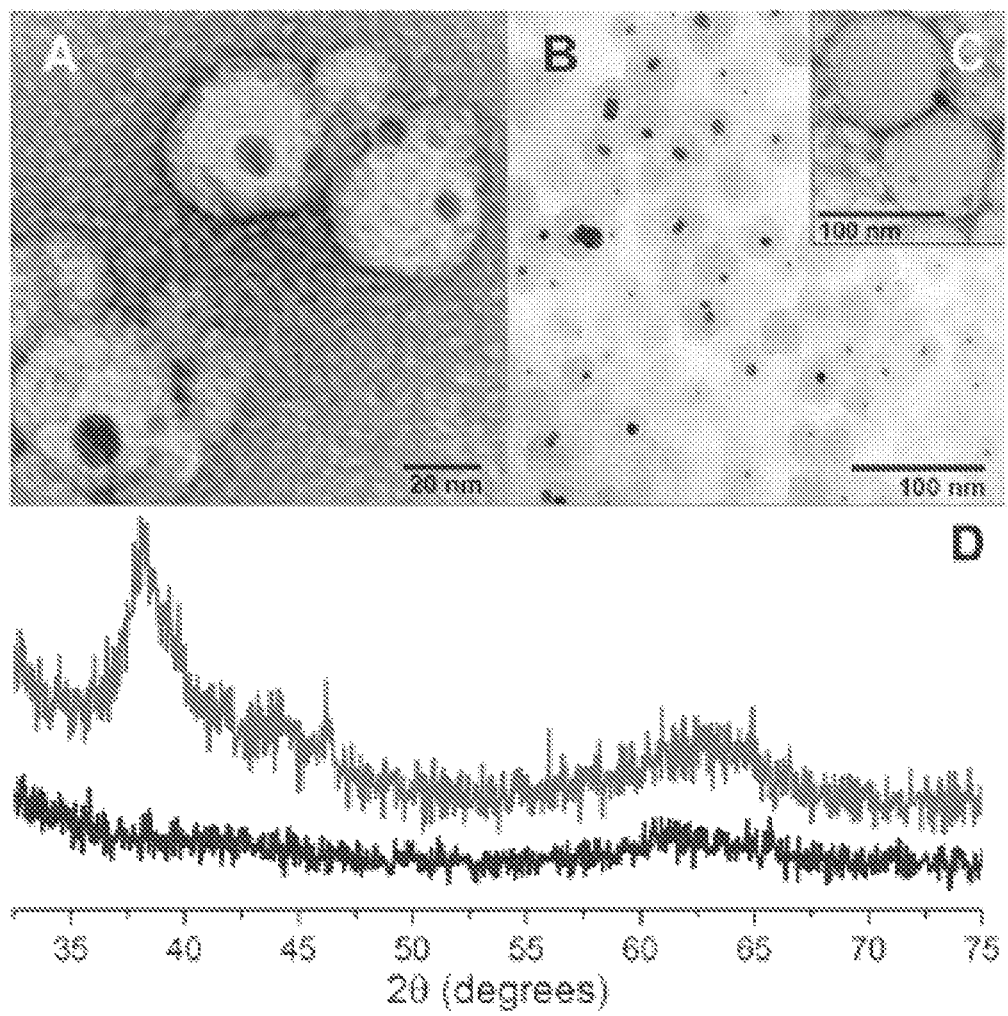
FIGS. 2A-2C are TEM images show polymer nanocapsules containing metal nanoparticles.
FIG. 2D shows X-ray diffraction patterns of nanocapsules containing silver nanoparticles (top) and blank nanocapsules (bottom).

TEM images show polymer nanocapsules containing metal nanoparticles (FIGS. 2A-C). Most nanocapsules found here are in the 40-120 nm range, consistent with previous studies.[6]

Statistical analysis of TEM data yielded the average size of silver nanoparticles to be 5.5±2.0 nm. Silver nanoparticles were further characterized by X-ray diffraction (FIG. 2D). A peak at 37° is characteristic of silver and is not present in the blank nanocapsules (FIG. 2D). The size of silver nanoparticles has been estimated by using the Debye-Scherrer formula.[11] The average particle size was calculated to be approximately 5 nm, in excellent agreement with TEM data.

Figure 3:
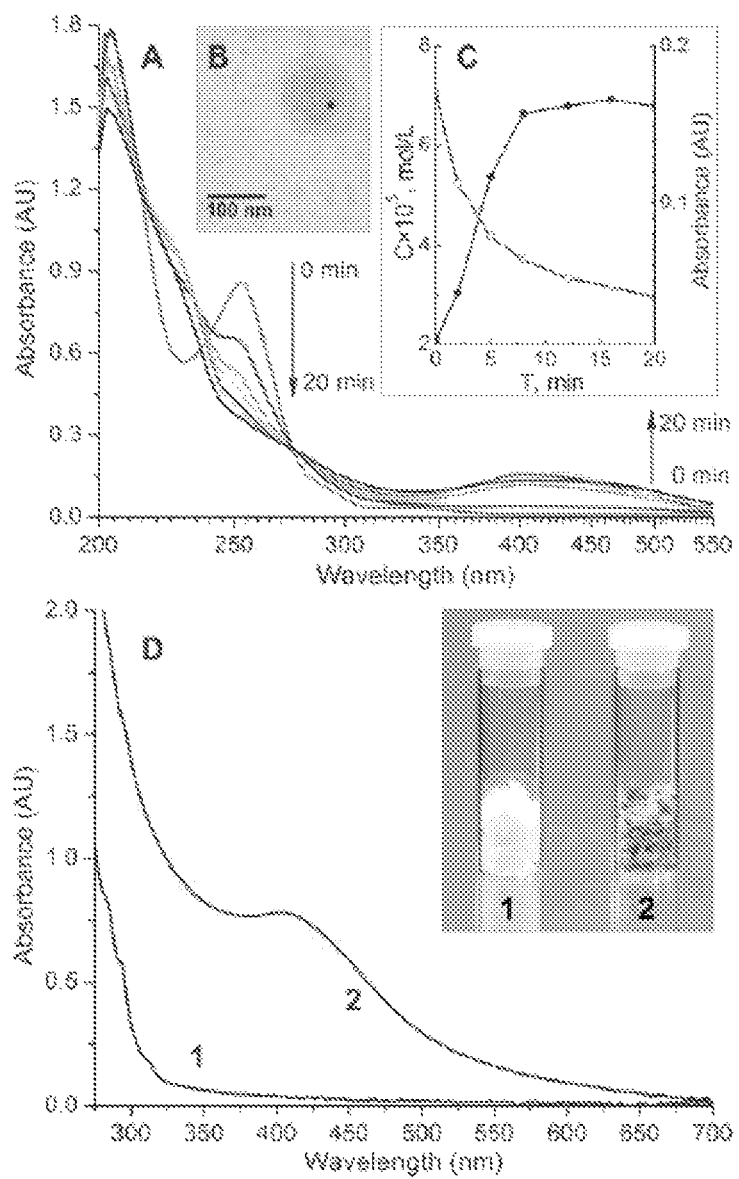
FIG. 3 shows UV and plasmon resonance analysis of liposomes containing $AgNO_3$. (A) UV spectra of liposomes containing $AgNO_3$ in the aqueous core and DMPA in the bilayer after varying exposure to UV light (0, 2, 5, 8, 12, 16, and 20 minutes). 150 ml aliquots were diluted in 2 ml of methanol to lyze liposomes and minimize light scattering. Gradually decreasing absorbance at 253 nm corresponds to the disappearance of DMPA; increased absorbance at 405 nm is from surface plasmon resonance in nanoparticles. (B) Liposome with a silver nanoparticle produced after 20 minutes of UV exposure in the presence of DMPA. (C) Increase of plasmon resonance (filled circles, right y-axis) and decrease of DMPA (empty circles, left y-axis, concentration in diluted methanol solutions) over time. (D) UV spectra of aqueous solutions of monomer-loaded liposomes containing AgNO3 and DMPA before (1) and after (2) exposure to UV irradiation. Inset: freeze-dried nanocapsules: empty (1) and containing entrapped silver nanoparticles (2).

The role of the free-radical photoinitiator in the formation of nanoparticles was investigated by studying nanoparticle templating in liposomes in the absence of monomers. Formation of nanoparticles was monitored using UV spectroscopy by increasing absorbance at 405 nm due to surface plasmon resonance (FIG. 3A). Nanoparticles begin to form within 1-2 minutes. After the first 10 minutes, there was little change in the absorption at 405 nm. The formation of liposome-templated nanoparticles was confirmed by TEM (FIG. 3B). In control experiments, performed under identical conditions in the absence of a free-radical initiator, no nanoparticles were found by TEM and UV analyses.

Disappearance of the initiator was monitored with UV spectroscopy by following absorption at 253 nm (FIG. 3A). The rate of nanoparticle growth correlates well with the rate of initiator disappearance (FIG. 3C). In our setup, the major portion of the initiator DMPA is located within the bilayer. Aqueous solubility of the initiator was estimated to be approximately $1.5\times10^{-4}$ M from the UV spectrum of the saturated aqueous solution of DMPA. This concentration is much lower than the concentration of silver ions used here (0.01 M). DMPA dissolved in water may seed the formation of nanoparticles. Most of the data in FIG. 3C come from DMPA associated with the bilayer. We have previously shown that the release of hydrophobic molecules from the bilayer is slow.[6f] Without wishing to be bound by any theory, it is likely that electron transfer at the water/bilayer interface contributes to the growth of nanoparticles.

The scope of simultaneous templating can be further expanded by using water-soluble initiators in addition to hydrophobic ones in order to independently vary concentration and nature of ions in the aqueous core and hydrophobic monomers in the bilayer. UV spectra reveal the presence of nanoparticles in the nanocapsules after the polymerization (FIG. 3D). Dried nanocapsules containing silver nanoparticles exhibit characteristic yellow color in contrast to empty nanocapsules (FIG. 3D, inset).

Based on sizes of nanocapsules and nanoparticles, it appears that less than 5% of nanocapsule volume is occupied by a nanoparticle and more than 95% of nanocapsule volume is available for co-entrapment of other species (e.g., drugs) or for allowing unhindered flow of analytes or substrates and products. Sizes of both nanocapsules and nanoparticles can be varied by changing the liposome diameter and concentration of metal salts. Bilayer-templated nanocapsules can be imprinted with nanopores having controlled size, density, and chemical environment.[6] Formation of nanopores is done using pore-forming templates that are co-dissolved with monomers within the bilayer interior and that are removed after the polymerization.[6] Functionalization of nanopores opens opportunities for regulating permeability of nano-capsules, including response to external stimuli. Controlled membrane transport can be useful for selective uptake of analytes and substrates or for the release of nanoparticles.

A simple method for obtaining metal nanoparticles entrapped in hollow polymer capsules with controlled permeability promises technological advances in diverse applications, such as creation of theranostic devices,[12] nanoreactors,[13] or sensors, e.g., surface-enhanced Raman scattering (SERS).[14]

In summary, we have demonstrated simultaneous synthesis of hollow polymer nanocapsules and entrapped silver nanoparticles. This method may be adapted to a broad range of metals and monomers. Newly prepared hybrid nanostructures open exciting opportunities for practical applications.

REFERENCES CITED 1. (a) S. J. Li and S. Gong, Adv. Funct. Mater., 2009, 19, 2601-2606; (b) J. P. Deng, W. C. Shih and C. Y. Mou, J. Phys. Chem. C, 2007, 111, 9723-9728; (c) Y. Deng, Y. Cai, Z. Sun, J. Liu, C. Liu, J. Wei, W. Li, C. Liu, Y. Wang and D. Zhao, J. Am. Chem. Soc., 2010, 132, 8466-8473.
2. (a) X. N. Xu, W. J. Brownlow, S. V. Kyriacou, Q. Wan and J. J. Viola, Biochemistry, 2004, 43, 10400-10413; (b) W. Sun, G. Wang, N. Fang and E. S. Yeung, Anal. Chem., 2009, 81, 9203-9208; (c) C. J. Murphy, A. M. Gole, S. E. Hunyadi, J. W. Stone, P. N. Sisco, A. Alkilany, B. E. Kinard and P. Hankins, Chem. Commun., 2008, 544-557.
3. T. Huang, P. D. Nallathamby and X. N. Xu, J. Am. Chem. Soc., 2008, 130, 17095-17105.
4. (a) J.-H. Park, G. von Maltzahn, E. Ruoslahti, S, N. Bhatia and M. J. Sailor, Angew. Chem., Int. Ed., 2008, 47, 7284-7288; (b) G. Gopalakrishnan, C. Danelon, P. Izewska, M. Prummer, P.-Y. Bolinger, I. Geissbuhler, D. Demurtas, J. Dubochet and H. Vogel, Angew. Chem., Int. Ed., 2006, 45, 5478-5483; (c) B. Dubertret, P. Skourides, D. J. Norris, V. Noireaux, A. H. Brivanlou and A. Libchaber, Science, 2002, 298, 1759-1762.
5. (a) M. Kim, K. Sohn, H. B. Na and T. Hyeon, Nano Lett., 2002, 2, 1383-1387; (b) K. M. Yeo, J. Shin and I. S. Lee, Chem. Commun., 2010, 46, 64-66.
6. (a) S. A. Dergunov, B. Miksa, B. Ganus, E. Lindner and E. Pinkhassik, Chem. Commun., 2010, 46, 1485-1487; (b) S. Dergunov and E. Pinkhassik, Angew. Chem., Int. Ed., 2008, 47, 8264-8267; (c) D.C. Danila, L. T. Banner, E. J. Karimova, L. Tsurkan, X. Wang and E. Pinkhassik, Angew. Chem., Int. Ed., 2008, 47, 7036-7039; (d) S. Tekobo and E. Pinkhassik, Chem. Commun., 2009, 1112-1114; (e) S. A. Dergunov, K. Kesterson, W. Li, Z. Wang and E. Pinkhassik, Macromolecules, 2000, accepted; (f) L. T. Banner, D.C. Danila, K. Sharpe, M. Durkin, B. Clayton, B. Anderson, A. Richter and E. Pinkhassik, Langmuir, 2008, 24, 11464-11473.
7. (a) N. Poulain, E. Nakache, A. Pina and G. J. Levesque, J. Polym. Sci., 1996,34, 729-737; (b) J. Hotz and W. Meier, Langmuir, 1998, 14, 1031-1036; (c) C. Nardin, T. Hirt, J. Leukel and W. Meier, Langmuir, 2000, 16, 1035-1041; (d) J. Kurja, R. J. M. Noelte, I. A. Maxwell and A. I. German, Polymer, 1993, 34, 2045-2049; (e) C. A. McKelvey, E. W. Kaler, J. A. Zasadzinski, B. Coldren and H. T. Jung, Langmuir, 2000, 16, 8285-8290; (f) M. Jung, D. H. W. Huber, P. H. H. Bomans, P. M. Frederic, J. Meuldijk, A. M. van Herk, H. Fischer and A. I. German, Langmuir, 1997, 13, 6877-6880; (g) J. F. P. d. S. Gomes, A. F.-P. Sonnen, A. Kronenberger, J. Fritz, M. A. N. Coelho, D. Fournier, C. Fournier-Noel, M. Mauzac and M. Winterhalter, Langmuir, 2006, 22, 7755-7759.
8. (a) P. He and X. Zhu, Mater. Res. Bull., 2008, 43, 625-630; (b) K. Hong, D. S.Friend, C. G. Glabe and D. Papahadjopoulos, Biochim. Biophys. Acta, 1983, 732, 320-323; (c) V. P. Torchilin, Nat. Rev. Drug Discovery, 2005, 4, 145-160.
9. (a) H. Hada, Y. Yonezawa, A. Yoshida and A. Kurakake, J. Phys. Chem., 1976, 80, 2728-2731; (b) M. Sakamoto, M. Fujistuka and T. Majima, J. Photochem. Photobiol., C, 2009, 10, 33-56; (c) S. K. Ghosh, S. Kundu, M. Mandal, S, Nath and T. Pal, J. Nanopart. Res., 2003, 5, 577-587; (d) T. Itakura, K. Torigoe and K. Esumi, Langmuir, 1995, 11, 4129-4134; (e) M. Sangermano, Y. Yagci and G. Rizza, Macromolecules, 2007, 40, 8827-8829;
(f) K. Esumi, T. Matsumoto, Y. Seto and T. Yoshimura, J. Colloid Interface Sci., 2005, 284, 199-203.
10. (a) P.-L. Kuo and N. J. Turro, Macromolecules, 1987, 20, 1216-1221; (b) R. Schmidt, T. Zhao, J.-B. Green and D. J. Dyer, Langmuir, 2002, 18, 1281-1287.
11. A. L. Patterson, Phys. Rev., 1939, 56, 978-982.
12. J. Yang, C.-H. Lee, H.-J. Ko, J.-S. Suh, H.-G. Yoon, K. Lee, Y.-M. Huh and S. Haam, Angew. Chem., Int. Ed., 2007, 46, 8836-8839.
13. (a) X. Liu and A. Basu, J. Am. Chem. Soc., 2009, 131, 5718-5719; (b) J. Deng, Y. Yu, S. Dun and W. Yang, J. Phys. Chem. B, 2010, 114, 2593-2601; (c) X. Feng, C. Mao, G. Yang, W. Hou and J.-J. Zhu, Langmuir, 2006, 22, 4384-4389.
14. (a) D. Graham, K. Faulds and W. E. Smith, Chem. Commun., 2006, 4363-4371; (b) M. Sanles-Sobrido, W. Exner, L. Rodriguez-Lorenzo, B. Rodriguez-Gonzalez, M. A. Correa-Duarte, R. A. Alvarez-Puebla and L. M. Liz-Marzan, J. Am. Chem. Soc., 2009, 131, 2699-2705.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of preparing a metal nanoparticle entrapped in a polymer nanocapsule, the method comprising polymerizing monomers to form the polymer nanocapsule and simultaneously forming the metal nanoparticle.

2. The method of claim 1, wherein the monomers are polymerized using a free-radical initiator.

3. The method of claim 1, wherein the monomers are polymerized in a lipid bilayer.

4. The method of claim 3, wherein the lipid bilayer is a lipid bilayer of a liposome.

5. The method of claim 1, wherein the metal nanoparticle is a metal selected from the group consisting of silver, platinum, palladium, and gold.

6. The method of claim 1, wherein the metal nanoparticle is silver.

7. The method of claim 1, wherein the polymer nanocapsule is a copolymer of a styrene with divinylbenzene.

8. The method of claim 1, wherein the polymer nanocapsule is a copolymer of tert-butylstyrene with divinylbenzene.

9. A metal nanoparticle entrapped in a polymer nanocapsule, prepare according to the method of claim 1.

10. The metal nanoparticle entrapped in a polymer nanocapsule of claim 9, wherein the metal nanoparticle is a metal selected from the group consisting of silver, platinum, palladium, and gold.

11. The metal nanoparticle entrapped in a polymer nanocapsule of claim 10, wherein the metal nanoparticle is silver.

12. The metal nanoparticle entrapped in a polymer nanocapsule of claim 9, wherein the polymer nanocapsule is a copolymer of a styrene with divinylbenzene.

13. The metal nanoparticle entrapped in a polymer nanocapsule of claim 12, wherein the polymer nanocapsule is a copolymer of tert-butylstyrene with divinylbenzene.

14. A catalyst comprising a metal nanoparticle entrapped in a polymer nanocapsule according to claim 9.

15. A sensor comprising a metal nanoparticle entrapped in a polymer nanocapsule according to claim 9.

16. A method of performing a metal-catalyzed reaction, the method comprising contacting a reactant with a metal nanoparticle entrapped in a polymer nanocapsule according to claim 9.

17. A method of preparing a metal nanoparticle entrapped in a polymer nanocapsule, the method comprising:
 providing an aqueous phase containing vesicles, wherein the aqueous phase includes a metal salt and the vesicles comprise at least one monomer; and
 polymerizing the at least one monomer to form the polymer nanocapsule and simultaneously forming the metal nanoparticle entrapped in the polymer nanocapsule.

18. The method of claim 17, wherein the at least one monomer is polymerized in a lipid bilayer of the vesicles.

19. The method of claim 18, wherein the lipid bilayer is a lipid bilayer of a liposome.

20. The method of claim 16, wherein the metal nanoparticle is formed by free-radical reduction of a metal ion dissolved in an aqueous solvent phase.